(12) United States Patent
Shevchuk et al.

(10) Patent No.: US 9,345,722 B2
(45) Date of Patent: May 24, 2016

(54) PHARMACEUTICAL FORMULATIONS FOR THE TREATMENT OF ALZHEIMER'S DISEASE

(75) Inventors: Ihor Shevchuk, Yonkers, NY (US); Steven Dinh, Briarcliff Manor, NY (US)

(73) Assignee: EMISPHERE TECHNOLOGIES, INC., Roseland, NJ (US)

(*) Notice: Subject to any disclaimer, the term of this patent is extended or adjusted under 35 U.S.C. 154(b) by 586 days.

(21) Appl. No.: 12/375,007

(22) PCT Filed: Jul. 24, 2007

(86) PCT No.: PCT/US2007/074176
§ 371 (c)(1),
(2), (4) Date: Feb. 13, 2009

(87) PCT Pub. No.: WO2008/014232
PCT Pub. Date: Jan. 31, 2008

(65) Prior Publication Data
US 2010/0004310 A1    Jan. 7, 2010

Related U.S. Application Data

(60) Provisional application No. 60/833,541, filed on Jul. 24, 2006.

(51) Int. Cl.
*A61K 31/4025* (2006.01)
*A61K 31/704* (2006.01)
*A61K 9/70* (2006.01)
*A61K 31/401* (2006.01)
*A61K 31/20* (2006.01)
*A61K 9/00* (2006.01)

(52) U.S. Cl.
CPC ............ *A61K 31/704* (2013.01); *A61K 9/0014* (2013.01); *A61K 9/0053* (2013.01); *A61K 9/7023* (2013.01); *A61K 31/20* (2013.01); *A61K 31/401* (2013.01)

(58) Field of Classification Search
CPC ... A61K 31/704; A61K 31/401; A61K 31/20; A61K 9/7023; A61K 9/0014; A61K 9/0053
USPC ........................................................ 514/422
See application file for complete search history.

(56) References Cited

U.S. PATENT DOCUMENTS

| | | | | |
|---|---|---|---|---|
| 6,103,910 A | * | 8/2000 | Hertel et al. ................... | 548/523 |
| 2005/0147662 A1 | * | 7/2005 | Freeman, Jr. .................. | 424/451 |
| 2005/0148497 A1 | * | 7/2005 | Khan .............................. | 514/8 |

OTHER PUBLICATIONS

Golden. Demential and Alzheimer's Disease. Clinical & Health Affairs. Minnesota Medicine, Jan. 1995 vol. 78 pp. 25-29.*

* cited by examiner

*Primary Examiner* — Jennifer M Kim
(74) *Attorney, Agent, or Firm* — Blank Rome LLP

(57) ABSTRACT

The present invention relate to pharmaceutical formulations that include a CPHPC component and a delivery agent compound.

15 Claims, 5 Drawing Sheets

PHARMACEUTICAL FORMULATIONS FOR THE TREATMENT OF ALZHEIMER'S DISEASE

CROSS-REFERENCE TO PRIOR APPLICATIONS

This is a U.S. National Phase Application under U.S.C. §371 of International Patent Application No. PCT/US2007/74176 filed Jul. 24, 2007, which claims the benefit of U.S. Provisional Application No. 60/833,541, filed Jul. 24, 2006. The International Application published in English on Oct. 25, 2007 as WO 2008/014232 under Article 21(2).

FIELD OF THE INVENTION

The present invention relates to pharmaceutical formulations containing a delivery agent compound and an active agent for treating Alzheimer's disease.

BACKGROUND OF THE INVENTION

Conventional means for delivering drugs are often severely limited by biological, chemical, and physical barriers. Typically, these barriers are imposed by the environment through which delivery occurs, the environment of the target for delivery, and/or the target itself. Examples of physical barriers include the skin, lipid bi-layers and various organ membranes that are relatively impermeable to certain drugs but must be traversed before reaching a target, such as the circulatory system. Chemical barriers include, but are not limited to, pH variations in the gastrointestinal (GI) tract and degrading enzymes.

These barriers are of particular significance in the design of oral and transdermal delivery systems. Oral delivery of many drugs would be the route of choice for administration if not for biological, chemical, and physical barriers that prevent, restrict or reduce the passage of drugs. Transdermal delivery is also a desired method to deliver drugs that can pass through the skin. Among the numerous drugs that oral or transdermal delivery is desired include those which bind to amyloid and SAP, such as CPHPC and their salts or other drugs that treat Alzheimer's such as rivastigmine tartrate.

Amyloidosis is not a single disease but a term for diseases that share a common feature: the extracellular deposition of pathologic insoluble fibrillar proteins in organs and tissues. Amyloid fibrils in primary amyloidosis are fragments of immunoglobulin light chains. There are different proteins making up the amyloid fibrils in reactive (secondary) amyloidosis and familial amyloidosis, and therefore specific therapies designed to target the source of fibril-precursor production.

The final pathway in the development of amyloidosis is the production of amyloid fibrils in the extracellular matrix. The process by which precursor proteins produce fibrils appears to be multifactorial and to differ among the various types of amyloid. In AL amyloidosis, the demonstration that substitutions of particular amino acids at specific positions in the light-chain variable region occur at significantly higher frequencies than in nonamyloid immunoglobulins has led to the suggestion that these replacements destabilize light chains, increasing the likelihood of fibrillogenesis.

In ATTR amyloidosis production of inherently unstable variant monomers of transthyrethin, produced by the substitution of amino acids, may allow the protein to precipitate when provoked by physical or chemical stimuli, resulting in the deposition of amyloid in organs in both AL and ATTR amyloidosis. These patients do not have clinically apparent disease until midlife, despite the lifelong presence of abnormal transthyretin, and have rapid progression and deterioration.

In addition, systemic amyloidosis is associated with hemodialysis and localized forms of amyloidosis are associated with Alzheimer's disease, Type II Diabetes, Medullary Carcinoma of the Thyroid and atrial amyloid deposition.

The treatment of amyloidosis is directed both toward the affected organ and to the specific type of the disease. Nephrotic disease is treated with diuretic therapy and dialysis. Congestive heart failure requires increasing doses of diuretics as cardiac disease progresses or renal function worsens. A subgroup of patients may benefit from implantation of a cardiac pacemaker. Neuropathy and gastrointestinal involvement are treated symptomatically. Gastromotility agents may be of some benefit. In familial Mediterranean fever, a genetic disorder associated with a high incidence of AA amyloidosis, therapy with colchicine specifically treats the underlying disease and prevents amyloidosis.

AL amyloidosis may be treated with chemotherapy; however, the response rate and survival rates are low with treatment with melphalan and prednisone. High dose therapy may provide substantial improvements in amyloid-related organ disease (hepatic, gastrointestinal, and neurological). The majority of patients with renal or cardiac involvement will also respond, with improved plasma cells and clinical symptoms.

In the small proportion of patients with AL amyloidosis that is limited to the heart, death is sudden or due to rapidly progressive heart failure. Cardiac transplantation has been performed in a few such patients, but progression in other organs or recurrence in the transplanted heart has occurred.

A limited number of patients with AL amyloidosis who receive chemotherapy with the iodinated anthracycline 4'-iodo-4'-deoxydoxorubicin had clinical benefit, and in vitro studies showed binding to amyloid fibrils and reduction of new deposits, but no reduction in circulating light chains could be documented Liver transplantation and in a few patients with severe symptomatic cardiac involvement, combined liver and heart transplantation from a single donor has been performed with success.

Serum amyloid P compound, SAP, is found on the surface of all types of amyloid deposits, preventing the livers's ability to break down amyloid and its subsequent removal from the body. Drugs, such as CPHPC are being developed which may treat amyloidosis and diseases associated with deposition of amyloid.

CPHPC is currently an investigational drug used to sequester SAP and therefore reduce circulating amyloids and which may be successful for the treatment, or perhaps even cure of Alzheimer's disease. A goal of treatment is to reduce the amyloid level, increase excretion, but investigational studies indicate that CPHPC has poor oral bioavailability and would require administration via the parenteral route. Accordingly, there is a need for improved oral delivery systems for CPHPC which provide sufficient bioavailability to treat diseases associated with amyloid accumulation, such as Alzheimer's, Amyloidosis, and Diabetes. There is also a need for improved bioavailability of other active agents that treat Alzheimer's disease, such as rivastigmine tartrate.

SUMMARY OF THE INVENTION

The present invention provides oral and transdermal pharmaceutical compositions comprising a delivery agent compound and an active agent for treating Alzheimer's disease or a condition associated therewith. In a preferred embodiment, the active agent is a CPHPC component, and the delivery agent is SNAC or pegylated SNAC.

DETAILED DESCRIPTION OF THE INVENTION

Definitions

Figure 1:
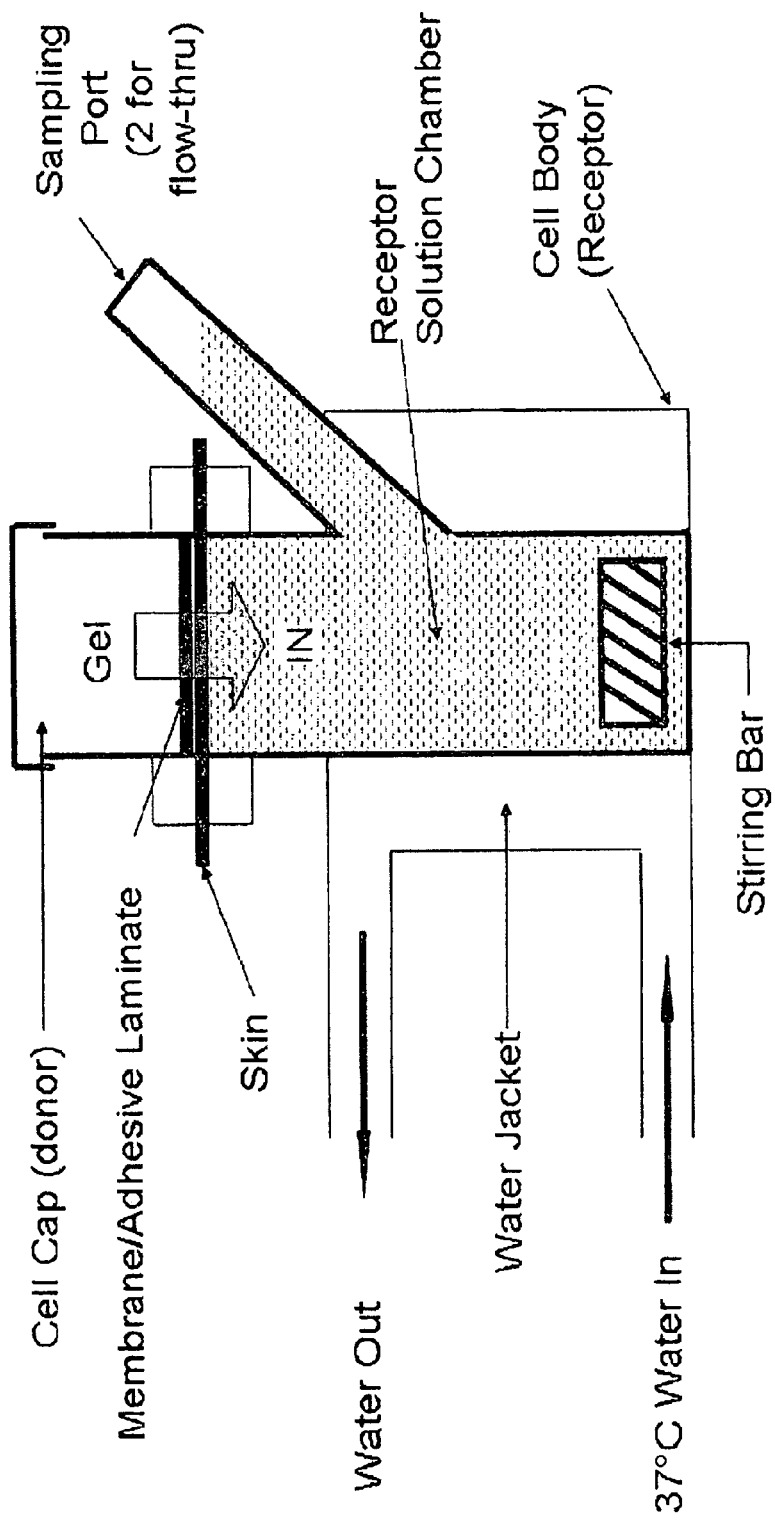
FIGS. 1 and 2 depict the flow-through diffusion cell system of Example 1.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the formulations can mean a range of up to 10%, preferably up to 5%.

The terms "alkyl", "alkenyl", "alkoxy", "alkylene", "alkenylene", "alkyl(arylene)", and "aryl(alkylene)" include, but are not limited to, linear and branched alkyl, alkenyl, alkoxy, alkylene, alkenylene, alkyl(arylene), and aryl(alkylene) groups, respectively.

The phrase "pharmaceutically acceptable" refers to compounds or compositions that are physiologically tolerable and do not typically produce an allergic or similar untoward reaction, such as gastric upset, dizziness and the like, when administered to a mammal.

An "effective amount of delivery agent" compound or "a therapeutically effective amount of a delivery agent compound refers to an amount of the delivery agent that enhances the absorption of a desired amount of a CPHPC component from, for example, the gastrointestinal tract or through the skin.

An "effective amount of a CPHPC component" or "a therapeutically effective amount of a CPHPC component" is an amount of the CPHPC component which is effective to treat or prevent a condition in a subject to whom it is administered over some period of time, e.g., provides a therapeutic effect during a desired dosing interval as included in the described pharmaceutical composition. The CPHPC component may be augmented with a second medication (such as galantamine, rivastigmine, donepezil, tacrine, memantine) to treat any of the disorders described in this application, such as Alzheimer's disease or amyloidosis.

As used herein, the term "treat" includes one or more of the following:

(a) arresting, delaying the onset (i.e., the period prior to clinical manifestation of a disorder) and/or reducing the risk of developing or worsening a disorder;

(b) relieving or alleviating at least one symptom of a disorder in a mammal, such as conditions associated with Alzheimer's disease (e.g., dementia); or (c) relieving or alleviating the intensity and/or duration of a manifestation of a disorder experienced by a mammal including, but not limited to, those which are in response to a given stimulus (e.g., pressure, tissue injury or cold temperature). The term "treat" also includes prophylactically preventing, curing, healing, alleviating, relieving, altering, remedying, ameliorating, improving, or affecting a condition (e.g., a disease), the symptoms of the condition, or the predisposition toward the condition.

The term "sustained release" as used herein refers to the release of an active ingredient over an extended period of time leading to relatively lower peak plasma concentrations and a prolonged $T_{max}$ as compared to "immediate release" formulations of the same active ingredient.

The term "Bioavailability" or "F" means the percentage of drug reaching systemic circulation. Generally, 100% bioavailability occurs with intravenous infusions since drug is delivered directly into the animal. Because of metabolism, first pass effects, food effect, and the like, oral bioavailability is generally lower. The delivery agents described herein have the ability to increase oral and transdermal bioavailability as compared to that particular active agent without the delivery agent.

The term "polymorph" refers to crystallographically distinct forms of a substance.

The term "hydrate" as used herein includes, but is not limited to, (i) a substance containing water combined in the molecular form and (ii) a crystalline substance containing one or more molecules of water of crystallization or a crystalline material containing free water.

The term "SNAC" as used herein refers to N-(8-[2-hydroxybenzoyl]-amino) caprylic acid and pharmaceutically acceptable salts thereof, including its monosodium and disodium salt. The term "SNAC free acid" or "the free acid of SNAC" refers to N-(8-[2-hydroxybenzoyl]-amino) caprylic acid. Unless otherwise noted, the term "SNAC" refers to all forms of SNAC, including all amorphous and polymorphic forms of SNAC, such as SNAC trihydrate and those described in U.S. Ser. Nos. 60/619,418 and 60/569,476, both of which are hereby incorporated by reference. The term "SNAC trihydrate" as used herein refers to a crystalline form of SNAC in which three molecules of water are associated with each molecule of SNAC. SNAC can be prepared by the procedures described in U.S. Pat. No. 5,650,386 and International Publication Nos. WO00/46182 and WO00/59863, which are hereby incorporated by reference.

The term "SNAD" as used herein refers to N-(8-[2-hydroxybenzoyl]-amino) decanoic acid and pharmaceutically acceptable salts thereof, including its monosodium salt. Unless otherwise noted, the term "SNAD" refers to all forms of SNAD, including all amorphous and polymorphic forms of SNAD.

The term "4-CNAB" as used herein refers to 4-[(4-chloro-2-hydroxy-benzoyl)amino]butanoic acid (also known as 4-[(2-hydroxy-4-chlorobenzoyl)amino]butanoate) and pharmaceutically acceptable salts thereof, including its sodium salt (e.g., monosodium salt). Unless otherwise noted, the term "4-CNAB" refers to all forms of 4-CNAB, including all amorphous and polymorphic forms of 4-CNAB. The term "sodium 4-CNAB" and "mono-sodium 4-CNAB" refer to monosodium 4-[(2-hydroxy-4-chlorobenzoyl)amino]butanoate, including anhydrous, monohydrate, and isopropanol solvates thereof and amorphous and polymorphic forms thereof (including those described in International Publication No. WO 03/057650 which is hereby incorporated by reference), unless otherwise indicated.

The term "solvate" as used herein includes, but is not limited to, a molecular or ionic complex of molecules or ions of a solvent with molecules or ions of a delivery agent or CPHPC salt.

The term "delivery agent" or "delivery agent compound" refers to any of the delivery agent compounds disclosed or incorporated by reference herein, with the proviso that all the delivery agents disclosed in U.S. Published Application No. 20050147662 and salts thereof, including the compounds shown below, are excluded as delivery agents compounds of the present invention:

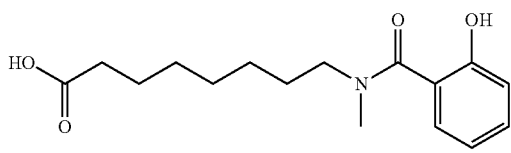

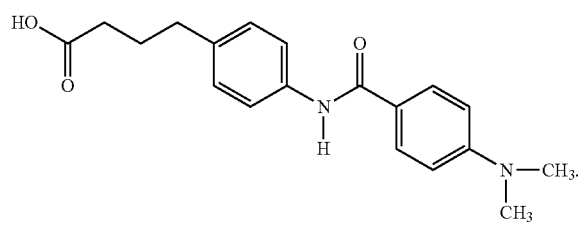

CPHPC Component

CPHPC refers to R-1-(6-(R-2-carboxy-pyrrolidin-1-yl)-6-oxo-hexanoyl)pyrrolidine-2-carboxylic acid, a drug that has been shown to sequester and promote the removal of a normal plasma protein called serum amyloid P component (SAP), thereby reducing circulating amyloids. The structure of the free acid of CPHC is:

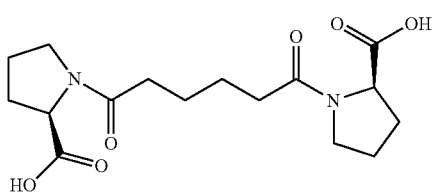 [SMILES: O=C(O)[C@H]1CCCN1C(=O)CCCCC(=O)N1CCC[C@@H]1C(=O)O]

As used herein the term CPHPC includes the free acid, and pharmaceutically acceptable salts thereof, including the sodium, disodium, halide, carbonate, acetate, triacetate, tartrate, oxalate, oxide, and hydroxide salts. The term CPHC also includes all anhydrous and hydrate forms of CPHPC.

As used herein, the term CPHPC component refers to CPHPC, as defined above, as well as analogs, active metabolites, prodrugs, racemates, and enantiomers of CPHPC.

Rivastigmine Component

Embodiments of the present invention also provide pharmaceutical compositions that include a rivastigmine component (e.g. rivastigmine tartrate) and a delivery agent compound (e.g. SNAC). The complete chemical name for rivastigmine tartrate is (S)—N-Ethyl-N-methyl-3-[1-(dimethylamino)ethyl]-phenyl carbamate hydrogen-(2R,3R)-tartrate and its structure is shown below:

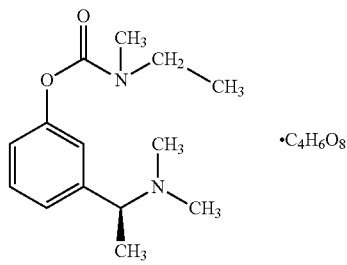 [SMILES: CCN(C)C(=O)Oc1cccc([C@H](C)N(C)C)c1 ; "·C4H6O8"]

Rivastigmine is a reversible inhibitor of the enzyme cholinesterase. Cholinesterase breaks down the neurotransmitter acetylcholine into choline and acetic acid. Inhibiting cholinesterase increases the time that acetylcholine is present and able to facilitate cognitive function. Thus, rivastigmine tartrate is thought to mediate senile dementia, Alzheimer's disease, Huntington's chorea, tardive dyskenesias, hyperkinesia, mania, acute confusion disorders, Down's syndrome, and Freidrich's ataxia.

Embodiments of the present invention provide a pharmaceutical composition comprising 0.1-25 mg of the rivastigmine component and an effective amount of the delivery agent compound. These compositions can be administered orally, parenterally, or transdermally, with oral and transdermal routes of administration preferred.

Rivastigmine tartrate is disclosed further in U.S. Pat. Nos. 4,948,807 and 5,602,176, both of which are hereby incorporated by reference in their entirety.

Other active agents that treat conditions associated may be included with delivery agents of the present invention, including active agents disclosed in U.S. Published Application Nos. 2006/0035946, 2006/0019930, 2006/0121038, and 2006/0034858. The active agents disclosed in European Published Application No. 0915088 and U.S. Pat. No. 7,045,499 may also be included with delivery agent compounds in compositions of the present invention. Each of these applications and patents are hereby incorporated by reference.

Delivery Agent Compounds

Suitable delivery agents include those having the following structure and pharmaceutically acceptable salts thereof:

$$2\text{-HO}—Ar—C(O)—NR^8—R^7—COOH \qquad \text{Formula (1)}$$

wherein

Ar is phenyl or naphthyl, optionally substituted with OH, halogen, $C_1$-$C_4$ alkyl. $C_1$-$C_4$ alkenyl, $C_1$-$C_4$ alkoxy or $C_1$-$C_4$ haloalkoxy;

$R^7$ is $C_4$-$C_{20}$ alkyl, $C_4$-$C_{20}$ alkenyl, phenyl, naphthyl ($C_1$-$C_{10}$ alkyl)phenyl, ($C_1$-$C_{10}$alkenyl)phenyl, ($C_1$-$C_{10}$alkyl) naphthyl, ($C_1$-$C_{10}$ alkenyl) naphthyl, phenyl($C_1$-$C_{10}$alkyl), phenyl($C_1$-$C_{10}$alkenyl), naphthyl($C_1$-$C_{10}$alkyl), or naphihyl ($C_1$-$C_{10}$alkenyl);

$R^8$ is hydrogen, $C_1$ to $C_4$ alkyl, $C_1$ to $C_4$ alkenyl, $C_1$ to $C_4$ alkoxy, $C_1$-$C_4$ or haloalkoxy;

$R^7$ is optionally substituted with $C_1$ to $C_4$ alkyl, $C_2$ to $C_4$ alkenyl, $C_1$ to $C_4$ alkoxy, $C_1$-$C_4$ haloalkoxy, —OH, —SH, and —$CO_2R^9$ or any combination thereof:

$R^9$ is hydrogen, $C_1$ to $C_4$ alkyl or $C_2$ to $C_4$ alkenyl; and $R^7$ is optionally interrupted by oxygen, nitrogen, sulfur or any combination thereof; with the proviso that the compounds are not substituted with an amino group in the position alpha to the acid group or salts thereof.

According to one embodiment, Ar is substituted with a halogen.

Preferably, $R^7$ is $C_4$-$C_{20}$ alkyl or phenyl($C_1$-$C_{10}$ alkyl). More preferably $R^7$ is $C_5$-$C_{10}$ alkyl or phenyl($C_2$ alkyl). Most preferably, $R^7$ is $C_7$-$C_9$ alkyl or phenyl($C_2$ alkyl).

Other suitable delivery agents include those having the following structure and pharmaceutically acceptable salts thereof:

$$2\text{-OH}-\text{Ar}-\text{C(O)}-\text{NH}-R^1\text{-}R^2 \qquad \text{Formula (2)}$$

wherein

Ar is phenyl or naphthyl;

Ar is optionally substituted with $C_1$-$C_4$ alkyl, $C_1$-$C_4$ alkoxy, $C_2$-$C_4$ alkenyl. $C_2$-$C_4$ alkynyl, aryl, aryloxy, a heterocyclic ring, $C_5$-$C_7$ carbocylic ring, halogen, —OH, —SH, $CO_2R^6$, —$NR^7R^8$, or —$N^+R^7R^8R^9Y^-$;

(a) $R^1$ is $C_1$-$C_{16}$ alkylene, $C_2$-$C_{16}$ alkenylene, $C_2$-$C_{16}$alkynylene, $C_6$-$C_{16}$ arylene, ($C_1$-$C_{16}$alkyl)arylene, or aryl ($C_1$-$C_{16}$alkylene);

$R^2$ is —$NR^3R^4$ or —$N^+R^3R^4R^5Y^-$:

$R^3$ and $R^4$ are independently hydrogen; oxygen; hydroxy; substituted or unsubstituted $C_1$-$C_{16}$alkyl; substituted or unsubstituted $C_1$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

$R^5$ is independently hydrogen; substituted or unsubstituted $C_1$-$C_{16}$ alkyl; substituted or unsubstituted $C_2$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

(b) $R^1$, $R^2$, and $R^5$ are as defined above; and $R^3$ and $R^4$ are combined to form a 5, 6 or 7-membered heterocyclic ring; or 5, 6 or 7-membered heterocyclic ring substituted with a $C_1$-$C_6$alkyl, $C_1$-$C_6$ alkoxy, aryl, aryloxy, oxo group or carbocyclic ring; or (c) $R^2$ and $R^5$ are as defined above; and $R^1$ and $R^3$ are combined to form a 5, 6 or 7-membered heterocyclic ring; or 5, 6 or 7-membered heterocyclic ring substituted with a $C_1$-$C_6$alkyl, alkoxy, aryl, aryloxy, or oxo group or carbocyclic ring;

$R^4$ is hydrogen; oxygen; hydroxy; substituted or unsubstituted $C_1$-$C_{16}$ alkyl; substituted or unsubstituted $C_2$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

$R^6$ is hydrogen; $C_1$-$C_4$ alkyl; $C_1$-$C_4$ alkyl substituted halogen or —OH; $C_2$-$C_4$ alkenyl; or $C_2$-$C_4$ alkenyl substituted halogen or —OH;

$R^7$, $R^8$, and $R^9$ are independently hydrogen; oxygen; $C_1$-$C_4$ alkyl; $C_1$-$C_4$ alkyl substituted with halogen or —OH; $C_2$-$C_4$ alkenyl; or $C_2$-$C_4$ alkenyl substituted with halogen or —OH; and Y is halogen, hydroxide, sulfate, nitrate, phosphate, alkoxy, perchlorate, tetrafluoroborate, or carboxylate. A non-limiting example of a suitable carboxylate is acetate.

The term "substituted" as used herein with respect to the compounds of formula (2) includes, but is not limited to, hydroxyl and halogen.

In one embodiment, Ar is unsubstituted phenyl or phenyl substituted with one or more of $C_1$-$C_4$ alkyl, $C_1$-$C_4$ alkoxy, or halogen. More preferably, Ar is a phenyl substituted with methoxy, Cl, F or Br, and even more preferably, Ar is a phenyl substituted with Cl.

In another embodiment, $R^1$ is $C_1$-$C_{12}$ alkyl, $C_2$-$C_8$ alkyl, $C_2$-$C_6$ alkyl, or $C_6$ alkyl.

In another embodiment. $R^3$ and $R^4$ are independently H or $C_1$-$C_2$ alkyl; or further $R^3$ and $R^4$ are not both H; or further $R^3$ and $R^4$ are independently methyl or ethyl; and more preferably $R^3$ and $R^4$ are both methyl.

Other suitable delivery agents include those having the following structure and pharmaceutically acceptable salts thereof:

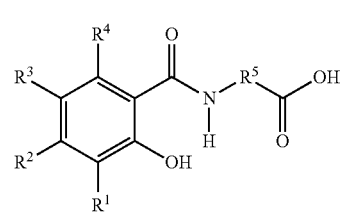

Formula (3)

wherein $R^1$, $R^2$, $R^3$, and $R^4$ are independently hydrogen. —OH, —$NR^6R^7$, halogen, $C_1$-$C_4$ alkyl, or $C_1$-$C_4$ alkoxy;

$R^5$ is a substituted or unsubstituted $C_2$-$C_{16}$ alkylene, substituted or unsubstituted $C_2$-$C_{16}$ alkenylene, substituted or unsubstituted $C_1$-$C_{12}$ alkyl(arylene), or substituted or unsubstituted aryl($C_1$-$C_{12}$ alkylene); and $R^6$ and $R^7$ are independently hydrogen, oxygen, or $C_1$-$C_4$ alkyl.

The term "substituted" as used with respect to formula (3) includes, but is not limited to, substitution with any one or any combination of the following substituents: halogens, hydroxide, $C_1$-$C_4$ alkyl, and $C_1$-$C_4$ alkoxy.

Other suitable delivery agents include those having the following structure and pharmaceutically acceptable salts thereof:

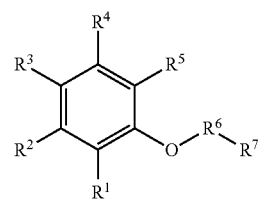

Formula (4)

wherein (a) $R^1$, $R^2$, $R^3$, and $R^4$ are independently H, —OH, halogen, $C_1$-$C_4$ alkyl, $C_1$-$C_4$ alkenyl, $C_1$-$C_4$alkoxy, —C(O)$R^8$, —$NO_2$, —$N^9R^{10}$, or —$N^+R^9R^{10}R^{11}(Y^-)$;

$R^8$ is hydrogen, —OH, $C_1$-$C_6$ alkyl, $C_1$-$C_4$ alkyl substituted with halogen or —OH, $C_2$-$C_4$ alkenyl unsubstituted or substituted with halogen or —OH, or —$NR^{14}R^{15}$;

$R^9$, $R^{10}$, and $R^{11}$ are independently hydrogen, oxygen. $C_1$-$C_4$ alkyl unsubstituted or substituted with halogen or —OH, $C_2$-$C_4$ alkenyl unsubstituted or substituted with halogen or —OH;

Y is halide, hydroxide, sulfate, nitrate, phosphate, alkoxy, perchlorate, tetrafluoroborate, carboxylate, mesylate, fumerate, malonate, succinate, tartrate, acetate, gluconate, maleate;

$R^5$ is H, —OH, —NO$_2$, halogen, CF$_3$, —NR$^{14}$R$^{15}$, —N$^+$R$^{14}$R$^{15}$R$^{16}$(Y$^-$), amide, $C_1$-$C_{12}$alkoxy, $C_1$-$C_{12}$ alkyl, $C_2$-$C_{12}$ alkenyl, carbamate, carbonate, urea, or —C(O)R$^{22}$; $R^5$ is optionally substituted with halogen, —OH, —SH, or —COOH; $R^5$ is optionally interrupted by O, N, S, or —C(O)—;

$R^{14}$, $R^{15}$, and $R^{16}$ are independently H or $C_1$-$C_{10}$ alkyl;

$R^{22}$ is H, $C_1$-$C_6$ alkyl, —OH, —NR$^{14}$R$^{15}$;

$R^6$ is substituted or unsubstituted $C_1$-$C_{16}$ alkylene, $C_2$-$C_{16}$ alkenylene, $C_2$-$C_{16}$ alkynylene, $C_5$-$C_{16}$ arylene, ($C_1$-$C_{16}$ alkyl) arylene or aryl($C_1$-$C_{16}$alkylene); $R^6$ is optionally substituted with $C_1$-$C_7$ alkyl or $C_1$-$C_7$ cycloalkyl:

$R^7$ is —NR$^{18}$R$^{19}$ or —N$^+$R$^{18}$R$^{19}$R$^{20}$Y$^-$;

$R^{18}$ and $R^{19}$ are independently hydrogen, oxygen, hydroxy, substituted or unsubstituted $C_1$-$C_{16}$ alkyl, substituted or unsubstituted $C_2$-$C_{16}$ alkenyl, substituted or unsubstituted $C_2$-$C_{16}$alkynyl, substituted or unsubstituted aryl, substituted or unsubstituted alkylcarbonyl (e.g. substituted or unsubstituted ($C_{1-6}$ alkyl)carbonyl), substituted or unsubstituted arylcarbonyl, substituted or unsubstituted alkanesulfinyl (e.g. substituted or unsubstituted ($C_{1-6}$alkane)sulfinyl), substituted or unsubstituted arylsulfinyl, substituted or unsubstituted alkanesulfonyl (e.g. substituted or unsubstituted ($C_{1-6}$ alkane)sulfonyl), substituted or unsubstituted arylsulfonyl, substituted or unsubstituted alkoxycarbonyl (e.g. substituted or unsubstituted ($C_{1-6}$ alkoxy)carbonyl), or substituted or unsubstituted aryloxyccarbonyl, or substituted or unsubstituted $C_5$-$C_7$ heterocyclic ring (i.e., 5, 6, or 7-membered heterocyclic ring), wherein the substitutions may be halogen or —OH; and $R^{20}$ is independently hydrogen, substituted or unsubstituted $C_1$-$C_{16}$ alkyl, substituted or unsubstituted $C_2$-$C_{16}$alkenyl, substituted or unsubstituted $C_2$-$C_{16}$alkynyl, substituted or unsubstituted aryl, substituted or unsubstituted alkylcarbonyl (e.g. substituted or unsubstituted ($C_{1-6}$ alkyl)carbonyl), substituted or unsubstituted arylcarbonyl, substituted or unsubstituted alkanesulfinyl (e.g. substituted or unsubstituted ($C_{1-6}$alkane)sulfinyl), substituted or unsubstituted arylsulfinyl, substituted or unsubstituted alkanesulfonyl (e.g. substituted or unsubstituted ($C_{1-6}$alkane)sulfonyl), substituted or unsubstituted arylsulfonyl, substituted or unsubstituted alkoxycarbonyl (e.g. substituted or unsubstituted ($C_{1-6}$alkoxy)carbonyl), or substituted or unsubstituted aryloxycarbonyl; or (b) $R^1$-$R^{16}$ and $R^{20}$ are as defined above; and $R^{18}$ and $R^{19}$ combine to form a 5, 6, or 7-membered heterocyclic ring optionally interrupted with an oxo group and unsubstituted or substituted with $C_1$-$C_6$ alkyl. $C_1$-$C_6$ alkoxy, aryl, aryloxy, or carbocyclic ring.

According to one embodiment, $R^7$ is morpholino, morpholinium salt, or diethanolamino.

According to another embodiment, $R^6$ is a $C_1$-$C_{16}$ alkylene and $R^7$ is morpholino or a morpholinium salt. Preferably, $R^6$ is $C_4$-$C_{12}$ alkylene, such as an unsubstituted $C_4$-$C_{12}$alkylene. More preferably, $R^6$ is $C_4$-$C_{10}$, $C_4$-$C_8$, or $C_6$-$C_8$ alkylene, such as an unsubstituted $C_4$-$C_{10}$, $C_4$-$C_8$, or $C_6$-$C_8$ alkylene. According to one embodiment, one of $R^1$-$R^5$ is hydroxy, for example, $R^1$ can be hydroxy.

According to yet another embodiment, when $R^6$ is a $C_1$-$C_{10}$ alkylene, at most one of $R^2$ and $R^4$ is halogen. According to another embodiment, $R^6$ is a $C_8$-$C_{16}$, $C_9$-$C_{16}$, $C_{10}$-$C_{16}$, or $C_{11}$-$C_{16}$ alkylene. For instance, $R^6$ may be a $C_8$, $C_9$, $C_{10}$, $C_{11}$, or $C_{12}$ alkylene (e.g., a normal $C_8$-$C_{12}$ alkylene). According to yet another embodiment, at most one of $R^1$ and $R^5$ is alkyl.

According to yet another embodiment, $R^1$ is hydroxy and $R^2$, $R^3$, $R^4$, and $R^5$ are independently hydrogen or halogen.

According to yet another embodiment, $R^2$ is hydroxy and $R^1$, $R^3$, $R^4$, and $R^5$ are independently hydrogen or halogen.

According to yet another embodiment, $R^3$ is hydroxy and $R^1$, $R^2$, $R^4$ and $R^5$ are independently hydrogen or halogen.

In a preferred embodiment, halogen is F, Cl or Br, more preferably F or Cl, and even more preferably Cl.

According to yet another embodiment, $R^6$ is $C_1$-$C_{16}$ alkylene, ($C_1$-$C_{16}$ alkyl) arylene or aryl($C_1$-$C_{16}$alkylene). More preferably $R^6$ is $C_1$-$C_{12}$ alkylene, more preferably $C_3$-$C_{10}$alkylene, more preferably $C_4$-$C_{10}$ or $C_4$-$C_8$ alkylene, and more preferably $C_6$-$C_8$ alkylene. More preferably, $R^6$ is unsubstituted.

According to yet another embodiment, $R^7$ is —NR$^{18}$R$^{19}$ and $R^{18}$ and $R^{19}$ are independently $C_1$-$C_4$ alkyl (e.g., methyl, ethyl, propyl, or butyl) substituted with —OH. In another embodiment, $R^7$ is —NR$^{18}$R$^{19}$ and $R^{18}$ and $R^{19}$ combine to form a six membered heterocyclic ring substituted with an oxo group.

According to one preferred embodiment, $R^1$ is hydrogen; $R^2$, $R^3$, and $R^4$ are independently hydrogen, halogen, —OH, or —OCH$_3$; $R^5$ is hydrogen, —OH, or —C(O)CH$_3$; $R^6$ is $C_1$-$C_{12}$ alkylene, and $R^7$ is NR$^{18}$R$^{19}$ wherein $R^{18}$ and $R^{19}$ combine to form a 5, 6, or 7 membered heterocyclic ring.

According to another preferred embodiment, one of $R^3$, $R^4$, and $R^5$ is hydroxy and the others are independently halogen or hydrogen; $R^1$ and $R^2$ are independently halogen or hydrogen; $R^6$ is $C_1$-$C_{16}$ alkylene; and $R^7$ is NR$^{18}$R$^{19}$ wherein $R^{19}$ and $R^{19}$ combine to form a 5, 6, or 7 membered heterocyclic ring. $R^6$ is preferably $C_6$-$C_{16}$, $C_6$-$C_{10}$, $C_9$-$C_{16}$, $C_{10}$-$C_{16}$ or $C_4$-$C_8$ alkylene, such as unsubstituted $C_6$-$C_{16}$, $C_6$-$C_{10}$, $C_8$-$C_{10}$, $C_{10}$-$C_{16}$, or $C_4$-$C_8$ alkylene. Preferably, $R^{18}$ and $R^{19}$ form a morpholino or imidazole.

In another preferred embodiment, $R^1$ is hydrogen; $R^2$, $R^3$ and $R^4$ are independently hydrogen, halogen, —OH, or —OCH$_3$; $R^5$ is hydrogen, —OH, or —C(O)CH$_3$; $R^6$ is $C_1$-$C_{12}$ alkylene; and $R^7$ is N$^+$R$^{18}$R$^{19}$R$^{20}$ (Y$^-$) wherein $R^{18}$ and $R^{19}$ are hydroxy substituted $C_1$-$C_{16}$; alkyl and $R^{20}$ is hydrogen.

In another preferred embodiment, $R^1$ is hydrogen; $R^2$, $R^3$, and $R^4$ are independently hydrogen, halogen, —OH, or —OCH$_3$; $R^5$ is hydrogen, —OH, or —C(O)CH$_3$; $R^6$ is $C_1$-$C_{12}$ alkylene; and $R^7$ is N$^+$R$^{18}$R$^{19}$R$^{20}$(Y$^-$) wherein $R^{18}$ and $R^{19}$ are hydroxy substituted $C_1$-$C_{16}$ alkyl and $R^{20}$ is hydrogen.

In another preferred embodiment, $R^1$, $R^2$, $R^4$, $R^5$ are independently halogen or hydrogen; $R^3$ is —OH, or —OCH$_3$; and $R^7$ is N$^+$R$^{18}$R$^{19}$R$^{20}$ (Y$^-$) wherein $R^{18}$ and $R^{19}$ are hydroxy substituted $C_1$-$C_{16}$alkyl and $R^{20}$ is hydrogen.

According to one preferred embodiment, $R^1$ is hydrogen; $R^2$, $R^3$, and $R^4$ are independently hydrogen, halogen, —OH, or —OCH$_3$; $R^5$ is hydrogen, —OH, or —C(O)CH$_3$; $R^6$ is $C_1$-$C_6$ alkylene or aryl substituted $C_1$-$C_{12}$ alkyl; and $R^7$ is —NR$^{18}$R$^{19}$ wherein $R^{18}$ and $R^{19}$ combine to form a 5, 6, or 7 membered heterocyclic ring or N$^+$R$^{18}$R$^{19}$R$^{20}$ (Y$^-$) wherein $R^{18}$ and $R^{19}$ ware hydroxy substituted $C_1$-$C_{16}$alkyl and $R^{20}$ is hydrogen.

In another preferred embodiment, the citrate salt of the delivery agent is used.

Other suitable delivery agents include those having the following structure and pharmaceutically acceptable salts thereof:

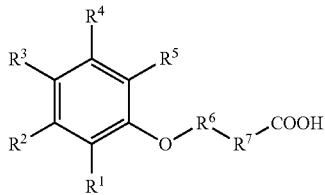

Formula (5)

wherein $R^1$, $R^2$, $R^3$, and $R^4$ are independently H, —OH, halogen, $C_1$-$C_4$ alkyl, $C_1$-$C_4$ alkenyl, $C_1$-$C_4$ alkoxy, —C(O)$R^8$, —NO$_2$, —NR$^9$R$^{10}$, or —N$^+$R$^9$R$^{10}$R$^{11}$(R$^{12}$)$^-$;

$R^5$ is H, —OH, —NO$_2$, halogen, —CF$_3$, —NR$^{14}$R$^{15}$, —N$^+$R$^{14}$R$^{15}$R$^{16}$ (R$^{13}$)$^-$, amide, $C_1$-$C_{12}$ alkoxy, $C_1$-$C_{12}$ alkyl, $C_2$-$C_{12}$ alkenyl, carbamate, carbonate, urea, or —C(O)$R^{18}$;

$R^5$ is optionally substituted with halogen, —OH, —SH, or —COOH;

$R^5$ is optionally interrupted by O, N, S, or —C(O)—;

$R^6$ is a $C_1$-$C_{12}$ alkylene, $C_2$-$C_{12}$ alkenylene, or arylene;

$R^6$ is optionally substituted with a $C_1$-$C_4$ alkyl, $C_1$-$C_4$ alkenyl, $C_1$-$C_4$ alkoxy, —OH, —SH, halogen, —NH$_2$, or —CO$_2$R$^8$;

$R^6$ is optionally interrupted by O or N;

$R^7$ is a bond or arylene;

$R^7$ is optionally substituted with —OH, halogen, —C(O)CH$_3$, —NR$^{10}$R$^{11}$, or —NR$^{10}$R$^{11}$R$^{12}$ (R$^{13}$)$^-$;

$R^8$ is H, $C_1$-$C_4$ alkyl, $C_2$-$C_4$ alkenyl, or —NH$_2$;

$R^9$, $R^{10}$, $R^{11}$ and $R^{12}$ independently H or $C_1$-$C_{10}$ alkyl;

$R^{13}$ is a halide, hydroxide, sulfate, tetrafluoroborate, or phosphate; and $R^{14}$, $R^{15}$ and $R^{16}$ are independently H, $C_1$-$C_{10}$ alkyl, $C_1$-$C_{10}$ alkyl substituted with —COOH, $C_2$-$C_{12}$ alkenyl, $C_2$-$C_{12}$ alkenyl substituted with —COOH, —C(O)$R^{17}$;

$R^{17}$ is —OH, $C_1$-$C_{10}$ alkyl, or $C_2$-$C_{12}$ alkenyl; and $R^{18}$ is H, $C_1$-$C_6$ alkyl, —OH, —NR$^{14}$R$^{15}$, or N$^+$R$^{14}$R$^{15}$R$^{16}$ (R$^{13}$).

According one embodiment.

(1) when $R^1$, $R^2$, $R^3$, $R^4$, and $R^5$ are H, and $R^7$ is a bond then $R^6$ is not a $C_1$-$C_6$, $C_9$ or $C_{10}$ alkyl;

(2) when $R^1$, $R^2$, $R^3$, and $R^4$ are H, $R^5$ is —OH, $R^7$ is a bond then $R^6$ is not a $C_1$-$C_3$ alkyl;

(3) when at least one of $R^1$, $R^2$, $R^3$, and $R^4$ is not H, $R^5$ is —OH, $R^7$ is a bond, then $R^6$ is not a $C_1$-$C_4$ alkyl;

(4) when $R^1$, $R^2$, and $R^3$ are H, $R^4$ is —OCH$_3$, $R^5$ is —C(O)CH$_3$, and $R^6$ is a bond then $R^7$ is not a $C_3$ alkyl; and (5) when $R^1$, $R^2$, $R^4$, and $R^5$ are H, $R^3$ is —OH, and $R^7$ is a bond then $R^6$ is not a methyl.

According one preferred embodiment, $R^1$ is hydrogen; $R^2$, $R^3$, and $R^4$ are independently hydrogen, halogen, —OH, or —OCHj; $R^5$ is hydrogen, —OH, or —C(O)CH$_3$; $R^6$ is $C_1$-$C_{12}$ alkylene, and $R^7$ is a bond or para-phenylene. $R^7$ is more preferably a $C_7$-$C_9$ alkyl.

According to another preferred embodiment, at least one of $R^1$, $R^2$, $R^3$, and $R^4$ is hydrogen, —C(O)CH$_3$, —OH, Cl, —OCH$_3$, F, or —NO$_2$. In one more preferred embodiment, $R^2$ is —C(O)CH$_3$, —OH, —OCH$_3$, or —Cl. In another more preferred embodiment, $R^3$ is Cl, —OCH$_3$, F, or —OH. In yet another more preferred embodiment, $R^4$ is —OCH$_3$ or —NO$_2$.

According to yet another preferred embodiment, $R^5$ is —C(O)CH$_3$, —OH, H, —CH═CHCH$_3$, —NH$_2$, —NO$_2$, —NHC(O)CH$_3$, —CH═CHCO$_2$H, —C(O)CH$_2$CH$_3$, —C(O)NH$_2$, —C(O)NHCH$_3$, —COOH, —C(O)NHCH$_2$CH$_3$, —C(O)NHCH(CH$_3$)$_2$, —OCH$_3$, —C(CH$_3$)$_2$OH, —C(OH)(CH$_3$)$_2$, or —CH(OH)CH$_3$.

According to yet another preferred embodiment, $R^6$ is a linear $C_1$-$C_{12}$ alkylene. More preferably, $R^6$ is —(CH$_2$)$_n$—, where n is an integer from 1 to 10.

According to yet another preferred embodiment, $R^4$ and $R^5$ are not alkyl or halogen.

According to yet another preferred embodiment, $R^7$ is para-phenylene or a bond.

According to yet another preferred embodiment, $R^6$ is —CH$_2$— and $R^7$ is phenylene and, more preferably para-phenylene. More preferably, at least one of $R^1$, $R^2$, $R^3$, and $R^4$ is hydrogen. More preferably, $R^5$ is —C(O)CH$_3$, —OH or —C(CH$_3$)$_2$OH.

According to yet another preferred embodiment, $R^7$ is a bond, $R^5$ is —OH, and $R^1$, $R^2$, $R^3$, and $R^4$ are hydrogen, $R^6$ is preferably $C_4$-$C_{12}$ alkylene and, more preferably, $C_4$-$C_9$ alkylene.

According to yet another preferred embodiment, $R^7$ is a bond, $R^5$ is —OH, and at least one of $R^1$, $R^2$, $R^3$, and $R^4$ is not hydrogen. $R^6$ is preferably $C_1$-$C_{12}$ alkylene, more preferably $C_5$-$C_{12}$ alkylene, and most preferably $C_5$-$C_9$ alkylene.

According to yet another preferred embodiment, $R^7$ is a bond, $R^7$ is —C(O)CH$_3$, and $R^1$, $R^2$, $R^3$, and $R^4$ are hydrogen. $R^6$ is preferably $C_1$-$C_{12}$ alkylene, more preferably $C_3$-$C_{12}$ alkylene, and most preferably $C_3$-$C_7$ alkylene.

According to yet another preferred embodiment, $R^7$ is a bond and $R^1$. $R^2$, $R^3$, $R^4$ and $R^5$ are hydrogen. Preferably, $R^6$ is $C_7$-$C_8$ alkylene.

According to yet another preferred embodiment, $R^7$ is a bond, $R^5$ is hydrogen, and at least one $R^1$, $R^2$, $R^3$, and $R^4$ are not hydrogen. $R^6$ is preferably $C_1$-$C_{12}$ alkylene, more preferably $C_4$-$C_9$ alkylene, and most preferably $C_7$-$C_3$ alkylene.

According to yet another preferred embodiment, $R^2$ is —OH. More preferably, $R^7$ is a bond and $R^5$ is hydrogen. Preferably, $R^6$ is $C_1$-$C_{12}$ alkylene, more preferably $C_3$-$C_9$ alkylene, and most preferably $C_7$ alkylene.

According to yet another preferred embodiment, $R^3$ is —OH. More preferably, $R^7$ is a bond and $R^5$ is hydrogen. $R^6$ is preferably $C_1$-$C_{12}$ alkylene, more preferably $C_3$-$C_9$ alkylene, and most preferably $C_7$ alkylene.

Other suitable delivery agents include those having the following structure and pharmaceutically acceptable salts thereof:

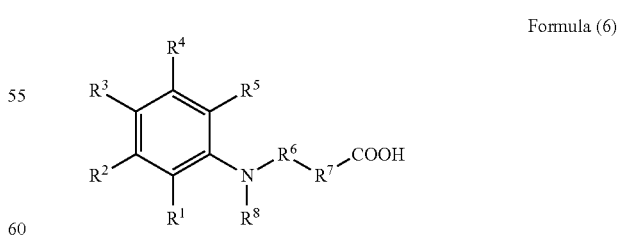

Formula (6)

wherein $R^1$, $R^2$, $R^3$, and $R^4$ are independently H, —OH, halogen, —OCH$_3$, —NR$^{10}$R$^{11}$ or —N$^+$R$^{10}$R$^{11}$R$^{12}$ (R$^{13}$)$^-$;

$R^5$ is H, —OH, —NO$_2$, —N$^+$R$^{14}$R$^{15}$, —N$^+$R$^{14}$R$^{15}$R$^{16}$ (R$^{13}$)$^-$, amide, $C_1$-$C_{12}$ alkoxy, $C_1$-$C_{12}$ alkyl, $C_2$-$C_{12}$ alkenyl, carbamate, carbonate, urea, or —C(O)$R^{18}$;

$R^5$ is optionally substituted with —OH, —SH, or —COOH;

$R^5$ is optionally interrupted by O, N, S, or —C(O)—;

$R^6$ is a $C_1$-$C_{12}$ alkylene, $C_1$-$C_{12}$ alkenylene, or arylene;

$R^6$ is optionally substituted with a $C_1$-$C_4$ alkyl, $C_2$-$C_4$ alkenyl, $C_1$-$C_4$ alkoxy, —OH, —SH, halogen, —NH$_2$, or —CO$_2$R$^9$;

$R^6$ is optionally interrupted by O or N;

$R^7$ is a bond or arylene;

$R^7$ is optionally substituted with —OH, halogen, —C(O)CH$_3$, —NR$^{10}$R$^{11}$ or —N$^+$R$^{10}$R$^{11}$R$^{12}$ (R$^{13}$)$^-$;

$R^8$ is H or $C_1$-$C_4$ alkyl;

$R^9$ is H, $C_1$-$C_4$ alkyl, or $C_2$-$C_4$ alkenyl;

$R^{10}$, $R^{11}$, and $R^{12}$ are independently H or $C_1$-$C_{10}$ alkyl;

$R^{13}$ is a halide, hydroxide, sulfate, tetrafluoroborate, or phosphate;

$R^{14}$, $R^{15}$, and $R^{16}$ are independently H, $C_1$-$C_{10}$ alkyl, $C_2$-$C_{12}$ alkenyl, O, or —C(O)R$^{17}$;

$R^{17}$ is —OH, $C_1$-$C_{10}$ alkyl, or $C_2$-$C_{12}$ alkenyl; and $R^{18}$ is —OH, $C_1$-$C_6$ alkyl, —NR$^{14}$R$^{15}$, —N$^+$R$^{14}$R$^{15}$R$^{16}$ (R$^{13}$)$^-$.

According to one embodiment, when $R^5$ is OCH$_3$ then $R^6$ is $C_1$-$C_8$ or $C_{10}$-$C_{12}$ alkyl.

According to a preferred embodiment, $R^5$ is not —OCH$_3$. More preferably, $R^5$ is not alkoxy.

According to another preferred embodiment. $R^1$, $R^2$, $R^3$, and $R^4$ are hydrogen, $R^5$ is —COOH, —C(O)NH$_2$, —C(O)CH$_3$, or —NO$_2$, $R^6$ is —(CH$_2$)—, and $R^7$ is a bond.

According to yet another preferred embodiment, $R^1$, $R^2$, $R^3$ and $R^4$ are hydrogen, $R^5$ is —C(O)NH$_2$, $R^6$ is —CH$_2$—, and $R^7$ is a para-phenylene.

According to one embodiment, the delivery agents of formula (6) have the formula:

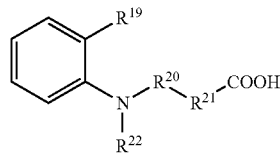

Formula (7)

wherein $R^{19}$ is —NO$_2$ or —C(O)R$^{23}$;

$R^{20}$ is a $C_1$-$C_{12}$ alkylene or $C_1$-$C_{12}$ alkenylene;

$R^{21}$ is a bond or arylene;

$R^{22}$ is H or $C_1$-$C_4$ alkyl; and $R^{23}$ is —OH, $C_1$-$C_6$ alkyl, or —NH$_2$.

Preferred delivery agents include, but are not limited to, SNAC, SNAD, 8-(N-2-hydroxy-5-chlorobenzoyl)aminocaprylic acid, 8-(N-2-hydroxy-4-methoxybenzoyl)-amino-caprylic acid, 4-CNAB, and pharmaceutically acceptable salts thereof.

According to one preferred embodiment, the delivery agent is SNAC or a pharmaceutically acceptable salt thereof. In one embodiment, the delivery agent is a sodium sail of SNAC. In another embodiment, the delivery agent is the monosodium salt of SNAC and can be, for example, any of the polymorphic forms of monosodium SNAC disclosed in U.S. Provisional Application No. 60/569,476, filed May 6, 2004, and U.S. Provisional Application No. 60/619,418, filed Oct. 15, 2004, both of which are hereby incorporated by reference. In yet another embodiment, the delivery agent is the disodium salt of SNAC.

According to another preferred embodiment, the delivery agent is SNAD or a pharmaceutically acceptable salt thereof.

In one embodiment, the delivery agent is a sodium salt of SNAD. In another embodiment, the delivery agent is the disodium salt of SNAD.

According to yet another preferred embodiment, the delivery agent is 4-CNAB or a pharmaceutically acceptable salt thereof. In one embodiment, the delivery agent is a sodium salt of 4-CNAB. The sodium 4-CNAB can be any of the amorphous and polymorphic forms described in International Publication No. WO 03/057650, which is hereby incorporated by reference.

Other suitable delivery agents of the present invention are described in U.S. Pat. Nos. 6,699,467, 6,663,898, 6,693,208, 6,693,073, 6,693,898, 6,663,887, 6,646,162, 6,642,411, 6,627,228, 6,623,731, 6,610,329, 6,558,706, 6,525,020, 6,461,643, 6,461,545, 6,440,929, 6,428,780, 6,413,550, 6,399,798, 6,395,774, 6,391,303, 6,384,278, 6,375,983, 6,358,504, 6,346,242, 6,344,213, 6,331,318, 6,313,088, 6,245,359, 6,242,495, 6,221,367, 6,180,140, 6,100,298, 6,100,285, 6,099,856, 6,090,958, 6,084,112, 6,071,510, 6,060,513, 6,051,561, 6,051,258, 6,001,347, 5,990,166, 5,989,539, 5,976,569, 5,972,387, 5,965,121, 5,962,710, 5,958,451, 5,955,503, 5,939,381, 5,935,601, 5,879,681, 5,876,710, 5,866,536, 5,863,944, 5,840,340, 5,824,345, 5,820,881, 5,811,127, 5,804,688, 5,792,451, 5,776,888, 5,773,647, 5,766,633, 5,750,147, 5,714,167, 5,709,861, 5,693,338, 5,667,806, 5,650,386, 5,643,957, 5,629,020, 5,601,846, 5,578,323, 5,541,155, 5,540,939, 5,451,410, 5,447,728, 5,443,841, and 5,401,516. Delivery agents of the present invention are also described in U.S. Published Application Nos. 20040110839, 20040106825, 20040068013, 20040062773, 20040022856, 20030235612, 20030232085, 20030225300, 20030198658, 20030133953, 20030078302, 20030072740, 20030045579, 20030012817, 20030008900, 20020155993, 20020127202, 20020120009, 20020119910, 20020102286, 20020065255, 20020052422, 20020040061, 20020028250, 20020013497, 20020001591, 20010039258, and 20010003001. Delivery agents of the present invention are also described in International Publication Nos. WO 2004/4104018, WO 2004080401, WO 2004062587, WO 2003/057650, WO 2003/057170, WO 2003/045331, WO 2003/045306, WO 2003/026582, WO 2002/100338, WO 2002/070438, WO 2002/069937, WO 02/20466, WO 02/19969, WO 02/16309, WO 02/15959, WO 02/02509, WO 01/92206, WO 01/70219, WO 01/51454, WO 01/44199, WO 01/34114, WO 01/32596, WO 01/32130, WO 00/07979, WO 00/06534, WO 00/06184, WO 00/59863, WO 00/59480, WO 00/50386, WO 00/48589, WO 00/47188, WO 00/46182, WO 00/40203, WO 99/16427, WO 98/50341, WO 98/49135, WO 98/34632, WO 98/25589, WO 98/21951, WO 97/47288, WO 97/31938, WO 97/10197, WO 96/40076, WO 96/40070, WO 96/39835, WO 96/33699, WO 96/30036, WO 96/21464, WO 96/12475, and WO 9612474. Each of the above listed U.S. patents and U.S. and International published applications are herein incorporated by reference.

The delivery agent compounds depicted as carboxylic acids may be in the form of the carboxylic acid or salts thereof. Suitable salts include, but are not limited to organic and inorganic salts, for example alkali-metal salts, such as sodium (e.g., monosodium and disodium salts), potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts. The salts may be mono- or multi-valent salts, such as monosodium salts and di-sodium salts. The salts may also be solvates, including ethanol solvates, and hydrates.

The delivery agent compounds depicted as amines may be in the form of the free amine or salts thereof. Suitable salts include, but are not limited to, organic and inorganic salts, for example sodium salts, sulfate salts, hydrochloride salts, phosphate salts, fluoride salts, carbonate salts, tartrate salts, oxalates, oxides, formates, acetate or citrate.

Salts of the delivery agent compounds of the present invention may be prepared by methods known in the art. For example, sodium salts may be prepared by dissolving the delivery agent compound in ethanol and adding aqueous sodium hydroxide.

Where the delivery agent has an amine moiety and a carboxylic acid moiety, poly amino acids and peptides comprising one or more of these compounds may be used. An amino acid is any carboxylic acid having at least one free amine group and includes naturally occurring and synthetic amino acids. Poly amino acids are either peptides (which are two or more amino acids joined by a peptide bond) or are two or more amino acids linked by a bond formed by other groups which can be linked by, e.g., an ester or an anhydride linkage. Peptides can vary in length from dipeptides with two amino acids to polypeptides with several hundred amino acids. One or more of the amino acids or peptide units may be acylated or sulfonated.

The delivery agent may contain a polymer conjugated to it such as described in International Publication No. WO 03/045306, which is hereby incorporated by reference. For example, the delivery agent and polymer may be conjugated by a linkage group selected from the group consisting of —NHC(O)NH—, —C(O)NH—, —NHC(O), —OOC—, —COO—, —NHC(O)—, —OC(O)NH—; —CH$_2$NH—NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond, with the proviso that the polymeric delivery agent is not a polypeptide or polyamino acid. The polymer may be any polymer including, but not limited to, alternating copolymers, block copolymers and random copolymers, which are safe for use in mammals.

Preferred polymers include, but are not limited to, polyethylene; polyacrylates; polymethacrylates; poly (oxyethylene); poly (propylene); polypropylene glycol; polyethylene glycol (PEG) (i.e. pegylated deliver agents); and derivatives thereof and combinations thereof. A particularly preferred delivery agent for transdermal applications include pegylated delivery agent compounds. The molecular weight of the polymer, e.g. the pegylated delivery agent compound typically ranges from about 100 to about 200,000 daltons. The molecular weight of the polymer preferably ranges from about 200 to about 10,000 daltons. In one embodiment, the molecular weight of the polymer ranges from about 200 to about 1,000 daltons and more preferably ranges from about 400 to about 800 daltons.

The compounds described herein may be derived from amino acids and can be readily prepared from amino acids by methods within the skill of those in the art, such as those described in International Publication Nos. WO96/30036, WO97/36480, WO00/06534. WO00/46812, WO00/50386, WO00/59863, WO 01/32596, and WO 00/07979 and U.S. Pat. Nos. 5,643,957, 5,650,386, and 5,866,536, all of which are incorporated by reference. For example, the compounds may be prepared by reacting the single amino acid with the appropriate acylating or amine-modifying agent, which reacts with a free amino moiety present in the amino acid to form amides. Protecting groups may be used to avoid unwanted side reactions as would be known to those skilled in the art. With regard to protecting groups, reference is made to T. W. Greene, *Protecting Groups in Organic Synthesis*, Wiley, New York (1981), the disclosure of which is hereby incorporated herein by reference.

The delivery agent compound may be purified by recrystallization or by fractionation on one or more solid chromatographic supports, alone or linked in tandem. Suitable recrystallization solvent systems include, but are not limited to, acetonitrile, methanol, ethanol, ethyl acetate, heptane, water, tetrahydrofuran, and combinations thereof. Fractionation may be performed on a suitable chromatographic support such as alumina, using methanol/n-propanol mixtures as the mobile phase; reverse phase chromatography using trifluoroacetic acia/acetonitrile mixtures as the mobile phase; and ion exchange chromatography using water or an appropriate buffer as the mobile phase. When anion exchange chromatography is performed, preferably a 0-500 mM sodium chloride gradient is employed.

In one embodiment, the following delivery agents are excluded as delivery agents of the present invention:

(a) 8-(2-hydroxyphenoxy)octyldiethanolamine ("HPOD"), and salts thereof, including the mesylate salt of HPOD and all other delivery ageni compounds disclosed in International Published Application No. WO 05/117854:

(b) all the delivery agent compounds disclosed in International Published Application No. WO 05/117854:

(c) all the delivery agent compounds disclosed in International Published Application No. WO 05/112633:

(d) all the delivery agent compounds disclosed in U.S. Published Application No. 2006/0078622; and (e) all the delivery agent compounds disclosed in U.S. Published Application No. 2006/0078623.

In one embodiment, the delivery agents compounds have a median particle size greater than about 900 or 1000 μm.

In one embodiment, delivery agent compounds are selected from the following group, including pharmaceutically acceptable salts thereof:

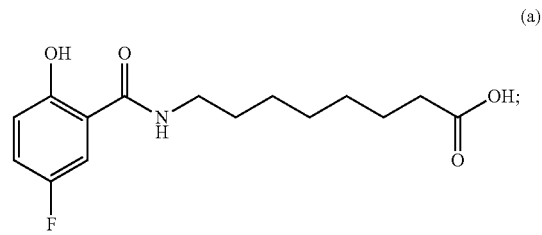

(a)

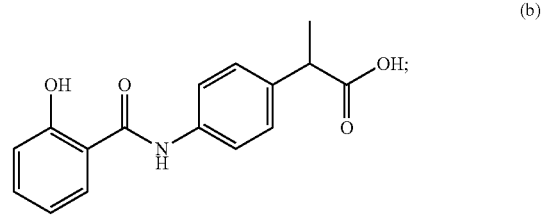

(b)

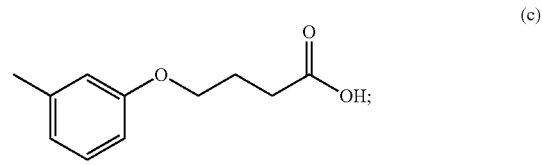

(c)

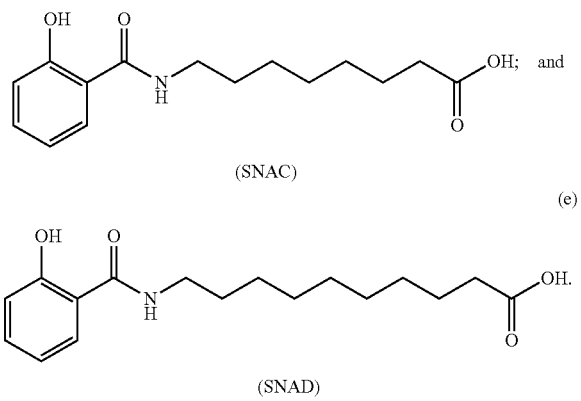

(d) (SNAC)

(e) (SNAD)

Transdermal Delivery Compositions Containing a CPHPC Component

Transdermal delivery bypasses first pass metabolism through the gastrointestinal tract, and provides a relatively flat plasma concentration thereby extending the half life of drugs with shorter durations of action. Transdermal delivery also provides easy application and discontinuance by removing the patch, and can improve compliance by providing multi-day or weekly administration.

One embodiment of the present invention provides a transdermal pharmaceutical formulation comprising a therapeutic amount of delivery agent compound (e.g. SNAC or Pegylated SNAC) and a therapeutic amount of a CPHPC component (e.g. the free acid of CPHPC).

Embodiments of the present invention provide a transdermal patch that includes a CPHPC component (e.g. the free acid of CPHPC), and a delivery agent compound (e.g. SNAC or Pegylated SNAC). Transdermal drug delivery systems are adhesive patches which are affixed to the skin. Drug delivery may be controlled by diffusion through the patch material and the drug containing matrix.

Transdermal patches may be composed of a backing, a drug reservoir (often with a rate controlling matrix and permeation enhancers), a rate controlling microporous membrane, and an adhesive. Transdermal drug delivery systems offer patients many advantages, including a more precise and constant drug concentration, lower steady state concentrations, reduced first pass effect, localized drug delivery, non invasive, less memory demanding, lack of movement restriction, easy drug administration, and decreased chance of infection. Transdermal patches are particularly preferred in the treatment of alzheimer's, since patient compliance with oral formulations is often low.

Preparation of transdermal patches is known in the art, and is described in U.S. Pat. Nos. 4,814,168; 4,946,853; 4,994,267; 4,994,278; 5,004,610; 5,016,652; 5,122,383; 5,164,190; 5,212,199; 5,223,261; 5,227,169; 5,232,438; 5,252,334; 5,300,291; 5,342,623; 5,344,656; 5,364,630; 5,393,529; 5,445,606; 5,462,745; 5,474,783; 5,474,783; 5,508,038; 5,633,008; 5,656,286; 5,656,286; 5,676, 968; 5,697,896; 5,770,219; 5,834,011; 5,843,014; 5,876,746; 5,891,868; 5,958,446; 5,958,446; 5,972,377; 6,024,976; 6,024,976; 6,165,497; 6,169,920; 6,171,294; 6,181,963; 6,195,582; 6,216,033; 6,317,626; 6,425,892; 6,582,737; 6,842,640; 6,881,208; 6,975,902; 7,018,370 and U.S. Pat. No. 7,027,859. Particular reference is drawn to the following 3M patents: U.S. Pat. No. 6,132,760; U.S. Pat. No. 6,136,807; U.S. Pat. No. 6,193,996; U.S. Pat. No. 6,893,655 and U.S. Pat. No. 6,796,429. Each of these applications are hereby incorporated by reference in their entirety.

The amount of the CPHPC component included in the pharmaceutical formulation is an amount effective to accomplish the purpose of the target indication. The amount of CPHPC in the pharmaceutical formulation typically is a pharmacologically, biologically, therapeutically, or chemically effective amount. However, the amount can be less than that amount when the pharmaceutical formulation is used in a dosage unit form of the present invention because the dosage unit form may contain a plurality of delivery agent/CPHPC pharmaceutical formulations or may contain a divided pharmacologically, biologically, therapeutically, or chemically effective amount. The total effective amount can then be administered in cumulative units containing, in total, an effective amount of the CPHPC component. Also, because the pharmaceutical formulations of the invention may deliver CPHPC more efficiently than formulations containing the CPHPC alone, lower amounts of CPHPC than those used in prior dosage unit forms or delivery systems can be administered to the subject, while still achieving the same blood levels and therapeutic effects.

One embodiment of the present invention provides a transdermal formulation that includes an effective amount of a delivery agent compound (e.g. SNAC) and a therapeutically effective amount of a CPHPC component which delivers a sustained amount of CPHPC, i.e. the transdermal formulation is a sustained release formulation.

In certain embodiments, the transdermal pharmaceutical formulation delivers from about 0.1 mg/day to about 50 mg/day of CPHC component, or about 0.3 mg/day, or about 0.84 mg/day, or about 5.6 mg/day, or about 6.3 mg/day, or about 9.6 mg/day or about 16.8 mg/day of CPHPC component.

In certain embodiments, the transdermal pharmaceutical formulation comprises a delivery agent compound and a CPHPC component and delivers a dose of CPHPC component from about 1 mcg/cm$^2$-day to about 500 mcg/cm$^2$-day or from about 8 mcg/cm$^2$ day or about 21 mcg/cm$^2$-day to about 5.139 mcg/cm$^2$-day, or about 6.158 mcg/cm$^2$-day, or about 241 mcg/cm$^2$-day or about 420 mcg/cm$^2$-day.

In one embodiment of the present invention, the transdermal pharmaceutical formulation is replaced on the patient daily. In yet another embodiment the transdermal pharmaceutical formulation is replaced every other day, or weekly, or monthly.

Yet another embodiment of the present invention provides a kit comprising a transdermal pharmaceutical formulation which includes a delivery agent compound (e.g. SNAC or pegylated SNAC) and a therapeutically effective amount of CPHC component. In certain embodiments, the kit may further include one or more tablets comprising a delivery agent compound and a therapeutically effective amount of a CPHPC component.

The transdermal delivery system may comprise a therapeutically effective amount of a delivery agent compound (e.g. SNAC or pegylated SNAC), a therapeutically effective amount of a CPHPC component (e.g. free acid of CPHPC) and a pharmaceutically acceptable solvent. In one embodiment, the pharmaceutically acceptable amount of solvent chosen from the group consisting of, a buffer around pH 8 (e.g. a phosphate pH 8.1 buffer containing phosphoric acid and/or phosphate salts), alcohols (e.g., ethanol), fatty acid/fatty acid ester blends, isopropylpalmitate, isopropylmystristate, mineral oil, silicone fluids, organic amine blends and plasticizers (e.g., triethyl citrate).

In one embodiment, the transdermal pharmaceutical composition comprises an effective amount of pegylated-SNAC, a therapeutically effective amount of the free acid of CPHPC and a pharmaceutically acceptable amount of a saturated pH 8.1 buffer. In yet another embodiment, the transdermal pharmaceutical composition comprises a therapeutically effective amount of the monosodium salt of SNAC, a therapeutically effective amount of the free acid of CPHPC and a pH 8.1 phosphate buffer.

Oral Delivery Compositions Containing a CPHPC Component

Another aspect of the present invention provides an oral pharmaceutical composition that includes a delivery agent compound (e.g. the monosodium or disodium salt of SNAC) and a CPHPC component (e.g. the free acid of CPHPC). The total amount of CPHPC to be used can be determined by methods known to those skilled in the art.

According to one embodiment, the pharmaceutical formulation includes a delivery agent compound and from about 0.01, 0.1, or 0.5 to about 1, 5, 10, or 20 mg/kg of the CPHPC component (e.g. the free acid of CPHPC). According to yet another embodiment, the pharmaceutical formulation includes a sufficient amount of a CPHPC component to provide a serum concentration, upon ingestion by a human, from about 0.01 ng/mL to about 6000 ng/ml, or from about 0.01 ng/mL to about 5500 mg/ml, or from 1000 ng/mL to about 3000 ng/mL In yet another embodiment, the oral pharmaceutical composition includes a CPHPC component and a delivery agent compound such that the oral formulation is capable of providing a serum concentration of CPHPC component from about 0.1 mg/kg to about 100 mg/mL, or more preferably about 0.25 mg/kg when administered to a human.

Yet another embodiment comprises an oral pharmaceutical composition that includes a therapeutically effective amount of a delivery agent compound (e.g. SNAC), a therapeutically effective amount of a CPHPC component to provide an oral bioavailability from about 3% or 10% to about 35% or 50%, more preferably about 30%.

The oral formulations of the present invention may be in the form of an immediate release formulation or a sustained release formulation. In one embodiment the oral formulation of the present invention provides a therapeutic peak level followed by a therapeutic sustained plasma level. For example, the oral formulation, may contain a delivery agent compound and a pharmaceutically acceptable amount of a CPHPC component, the formulation having an immediate release portion and a sustained release portion.

In yet another embodiment comprises an oral formulation which provides from about 0.01 mg/kg/day to about 10 mg/kg/day, more preferably about 0.25 mg/kg/day of CPHPC component.

The pharmaceutical formulations can include any one or combination of excipients, diluents, disintegrants, lubricants, fillers, plastieizers, colorants, flavorants, taste-masking agents, sugars, sweeteners, salts, and dosing vehicles, including, but not limited to, water, 1,2-propane diol, ethanol, olive oil, or any combination thereof.

The delivery agents facilitate the delivery of CPHPC, particularly in oral form, but are also be useful in intranasal, sublingual, intraduodenal, subcutaneous, buccal, imracolonic, rectal, vaginal, mucosal, pulmonary, transdermal, intradermal, parenteral, intravenous, intramuscular and ocular systems.

Methods of Treatment for the CPHC Component

The pharmaceutical formulations of the present invention are useful for administering CPHPC to mammals including, but not limited to, horses, rodents, cows, pigs, dogs, cats, primates, and particularly humans. The pharmaceutical formulation of the present invention can be administered to treat and/or prevent any disorder for which CPHPC is known to be capable of treating and/or preventing. Typically, an effective amount of the pharmaceutical formulation is administered to treat and/or prevent the desired disorder. Such disorders which can be treated by pharmaceutical compositions of the present invention include, but are not limited to, amyloidosis of all types (including atrial amyloid deposition, primary amyloidosis, secondary amyloidosis, AL amyloidosis and ATTR amyloidosis), diabetes, dementia, medullary carcinoma of the thyroid and Alzheimer's Disease.

According to another embodiment the pharmaceutical formulation includes other active agents which treat, cure, mitigate and/or prevent amyloidosis, diabetes type I, diabetes type II, Alzheimer's Disease, medullary carcinoma of the thyroid, or atrial amyloid deposition.

One embodiment of the present invention provides a method of sequestering SAP comprising an effective amount of the pharmaceutical formulation of the present invention to a subject in need thereof.

The following examples illustrates the invention without limitation. All parts are given by weight unless otherwise indicated.

EXAMPLES

The following examples illustrates the invention without limitation. All parts are given by weight unless otherwise indicated.

Example 1

CPHC was added to the solvents listed in Table 1 below to the point of saturation:

| Donor solution | CPHPC Concentration (mg/g) | Solvent | CPHPC Applied Dose (mg/cm2) |
|---|---|---|---|
| #1 | 239.2 | ethanolamine | 57.68 |
| #2 | 26.5 | 0.2 M pH 8.1 phosphate buffer (phosphoric acid and phosphate salts) | 10.65 |
| #3 | 16.6 | 0.2 M pH 8.1 phosphate buffer with pegylated SNAC (MW ~601) | 5.34 |
| #4 | 30.0 | 0.2 M pH 8.1 phosphate buffer with monosodium SNAC | 9.65 |
| #5 | 0.94 | pegylated SNAC (MW ~601) | 0.15 |
| #6 | 24.2 | Ethanolamine & free acid of SNAC (194 mg/g) | 3.89 |

Figure 2:
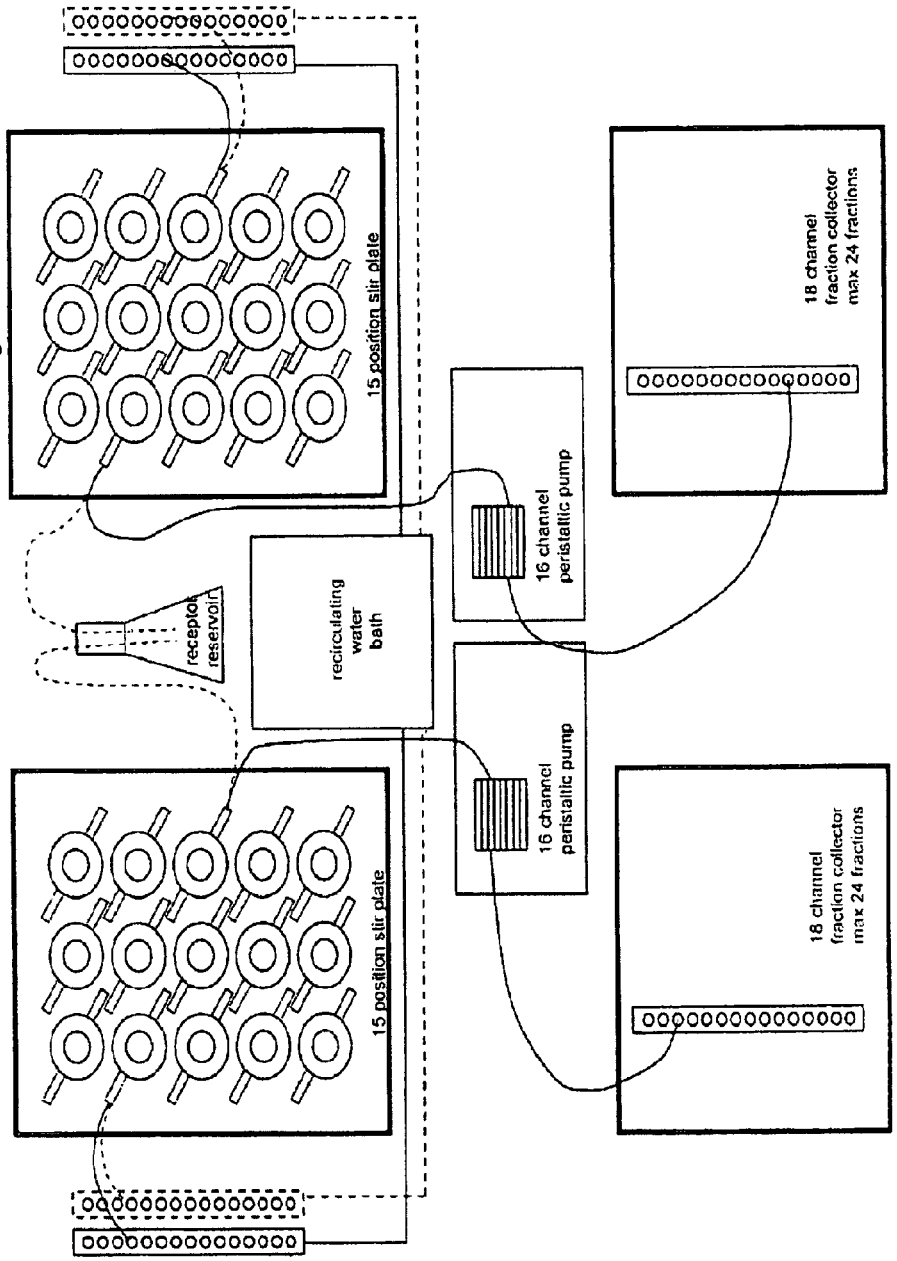

These solutions were applied to human cadaver skin with an applied dose of CPHC ranging from 0.15 mg/cm$^2$ to 57.68 mg/cm$^2$ as shown above in Table 1. The test method utilized a permeation cell. The cells are made with a definable surface area for permeation. The cells contain two chambers and a clamping mechanism to hold the cadaver skin positioned between the two cell chambers. The receptor was chosen to mimic the physiological conditions found beneath the membrane in-vivo (0.1M phosphate buffer at pH 7.4). The cells were kept at a constant 33° C. during the experiments. Calculation of the permeation rate (J) requires knowledge of the concentration (C) of the drug in the receptor chamber, the permeation area (A), sampling interval (t) and the receptor volume (V). The drug concentration in the receptor was determined by high performance liquid chromatography. The flow-through diffusion cell system shown in FIGS. 1 and 2.

CHPHC flux, cumulative CHPC delivery through the cadaver skin, calculated daily delivery of CPHC (based on a dosage size of about 25 cm$^2$, and lag time are shown below in Table 2:

TABLE 2

CPHPC Skin Permeation Results

| | donor solution | CPHPC flux ($J_{ss}$) (μg/cm²-hr) avg ± std. dev. | CV % | CPHPC (μg/cm²-day) cumulative | calculated (mg/day) 40 cm² | $t_{lag}$ (hr) |
|---|---|---|---|---|---|---|
| 1 | 239.2 mg/g in ethanolamine n = 5 | 10.4 ± 8.0 | 77 | 241 | 9.6 | <1 |
| 2 | sat. pH 8.1 buffer (26.5 mg/g) n = 4 | 1.3 ± 0.4 | 31 | 21 | 0.84 | <1 |
| 3 | Sat water/D12 29/71 (16.6 mg/g) n = 8 | 6.5 ± 4.8 | 74 | 158 | 6.3 | <1 |
| 4 | sat. pH 8.1 buffer w/SNAC (30.0 mg/g) n = 5 | 5.0 ± 1.3 | 26 | 139 | 5.6 | <1 |
| 5 | sat. D12 (0.94 mg/g) n = 3 | 0.5 ± 0.4 | 80 | 8 | 0.3 | <1 |
| 6 | ethanolamine + NAC n = 6 | 6.7 ± 3.6 | 53 | 420 | 16.8 | <1 |

Figure 3:
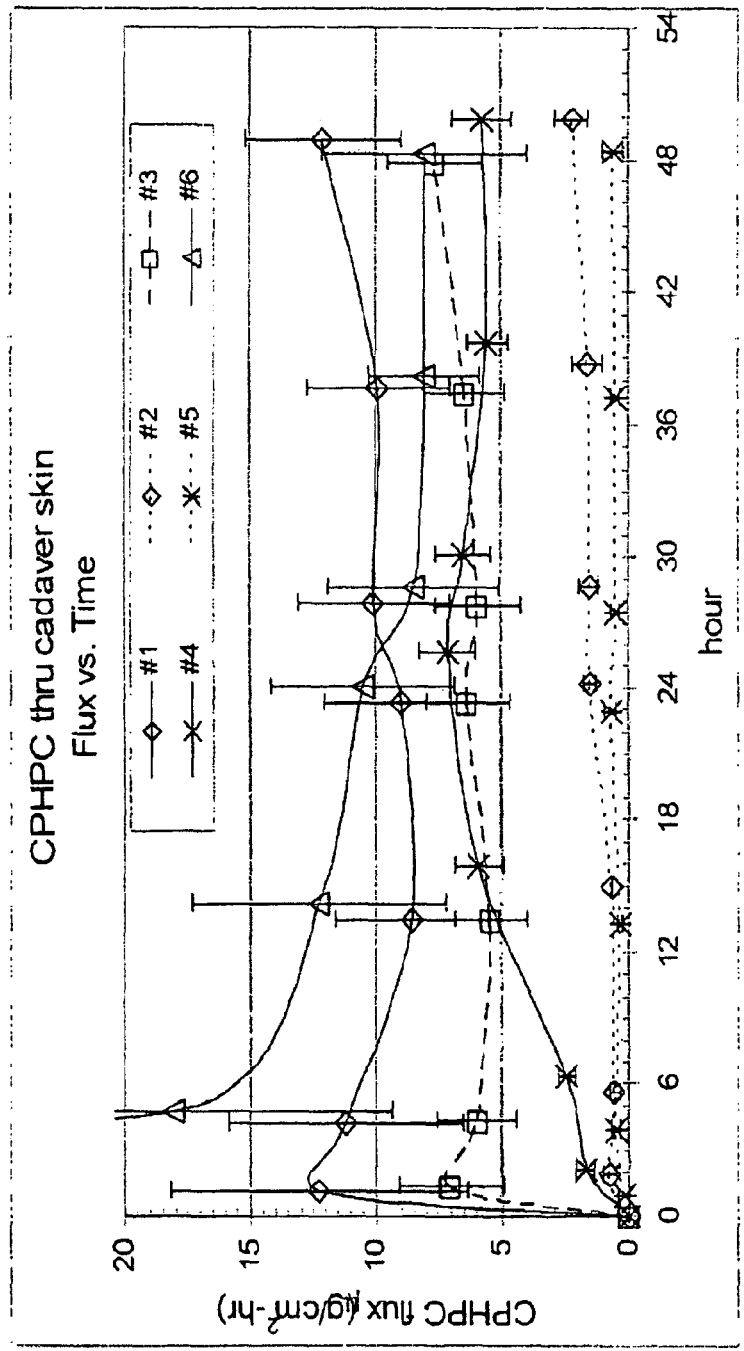
FIG. 3 is a graph showing the CPHPC flux following application of the CPHPC formulations of Example 1 to human cadaver skin over time.
Figure 4:
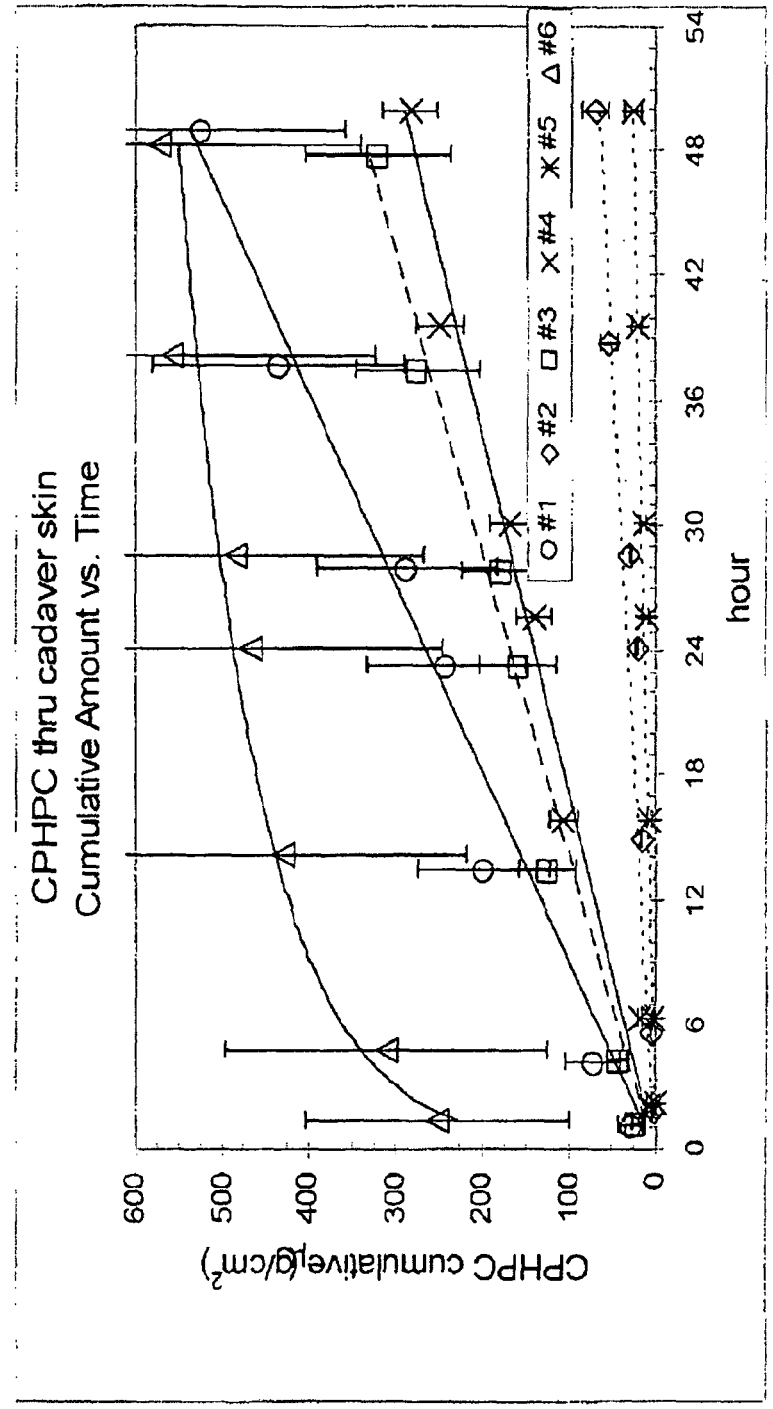
FIG. 4 is a graph showing the cumulative amount of CPHPC following application of the CPHPC formulations of Example 1 through the cadaver skin over time.

CPHPC flax over about 48 hours is also shown in FIG. 3. The cumulative amount CPHPC through the cadaver skin is also shown in FIG. 4.

Donor solution #1 with ethanolamine as a solvent contains significantly larger amounts of CPHPC since CPHPC is much more soluble in ethanolamine. Ethanolamine is a skin irritant, and is therefore not a likely candidate for a commercial embodiment. It is included to represent a theoretical maximum of CPHPC delivery.

Example 2

Oral Delivery of CPHPC in Rats

One group of rats were dosed by oral gavage a solution containing 200 mg/kg SNAC and 10 mg/kg CPHPC (Group 1). The dosing volume was 1 mL/kg. Two groups of rats also received, respectively, control arms of 10 mg/kg CPHPC alone via oral gavage (Group 2) and 0.2 mg/kg of CPHPC via IV (Group 3).

Serum CPHPC concentrations mg/ml) were measured over 40 minutes. The results are shown below in Table 3:

TABLE 3

| Group # | 0 min. | 5 min. | 10 min. | 20 min. | 40 min. |
|---|---|---|---|---|---|
| 1 (200 mg/kg SNAC and 10 mg/kg CPHPC via PO) | 0 ± 0 | 2962 ± 1210.24 | 5484.4 ± 525.81 | 2796.8 ± 400.03 | 1444.4 ± 218.56 |
| 2 (10 mg/kg CPHPC via PO) | 0 ± 0 | 1056.8 ± 107.12 | 1420.8 ± 171.34 | 666.8 ± 97.10 | 174.8 ± 14.96 |
| 3 (0.2 mg/kg of CPHPC via IV) | 0 ± 0 | 223.4 ± 19.49 | 228.8 ± 44.80 | 169.8 ± 26.18 | 65.4 ± 25.74 |

Figure 5:
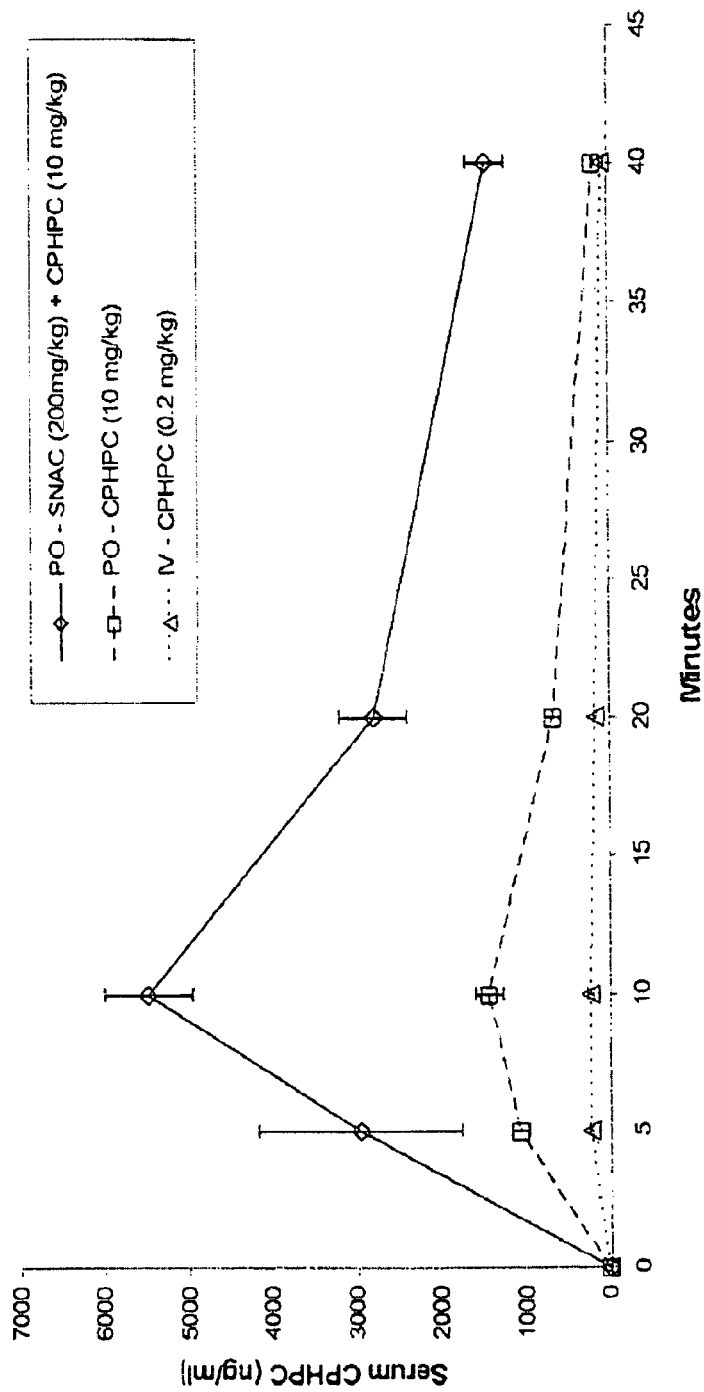
FIG. 5 is a graph of serum CPHPC following administration of an oral SNAC / CPHPC solution, an oral CPHPC solution, and an intravenous CPHPC solution to rats as described in Example 2 over time.

Results are also shown in FIG. 5.

The above mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:

1. A transdermal pharmaceutical composition comprising a delivery agent, CPHPC, and a solvent, wherein the delivery agent is selected from N-(8-[2-hydroxybenzoyl]amino)caprylic acid, pegylated-N-(8-[2-hydroxybenzoyl]amino)caprylic acid, and pharmaceutically acceptable salts thereof, the pharmaceutical composition is suitable for transdermal administration, and the pharmaceutical composition delivers a dose of CPHPC of between about 1 mcg/cm²/day and about 500 mcg/cm²/day.

2. The transdermal pharmaceutical composition of claim 1, wherein the solvent is selected from ethanolamine, a pH 8.1 buffer, deionized water, an alcohol, a fatty acid/fatty acid ester blend, isopropyl palmitate, isopropyl mystristate, mineral oil, a silicone fluid, an organic amine, a plasticizer, and combinations thereof.

3. The transdermal pharmaceutical composition of claim 1, wherein the delivery agent is N-(8-[2-hydroxybenzoyl]-amino) caprylic acid or a pharmaceutically acceptable salts thereof.

4. The transdermal pharmaceutical composition of claim 3, wherein the delivery agent is a sodium salt of N-(8-[2-hydroxybenzoyl]amino)caprylic acid.

5. The transdermal pharmaceutical composition of claim 1, wherein the pharmaceutical formulation provides sustained release of the CPHPC component.

6. A method of treating amyloid accumulation in a mammal in need thereof comprising transdermally administering to the mammal an effective amount of the pharmaceutical formulation of claim 1.

7. The method of claim 6, wherein the amyloid accumulation is due to Alzheimer's Disease.

8. A method of treating a disorder associated with excessive deposition of amyloid in a mammal comprising transdermally administering to the mammal an effective amount of the pharmaceutical formulation of claim 1.

9. A method of inhibiting amyloid deposition in a mammal with Alzheimer's Disease or Amyloidosis comprising transdermally administering to the mammal an effective amount of the pharmaceutical formulation of claim 1.

10. A method of treating amyloid deposition in a mammal with Alzheimer's Disease or Amyloidosis comprising transdermally administering to the mammal an effective amount of the pharmaceutical formulation of claim 1.

11. A method of reducing amyloid deposition in a mammal with Alzheimer's Disease or Amyloidosis comprising transdermally administering to the mammal an effective amount of the pharmaceutical formulation of claim 1.

12. A method for administering a CPHPC component to a mammal in need thereof comprising transdermally administering to the mammal the pharmaceutical formulation of claim 1.

13. A method of treating amyloid deposition in a mammal with diabetes, dementia or medullary carcinoma of the thyroid comprising transdermally administering to the mammal an effective amount of the pharmaceutical formulation of claim 1.

14. The transdermal pharmaceutical composition of claim 1, wherein the pharmaceutical composition delivers a dose of CPHPC of between about 8 mcg/cm$^2$/day and about 21 mcg/cm$^2$/day.

15. The transdermal pharmaceutical composition of claim 1, wherein the pharmaceutical composition delivers a dose of CPHPC of about 5.1 mcg/cm$^2$/day, about 6.2 mcg/cm$^2$/day, about 241 mcg/cm$^2$/day, or about 420 mcg/cm$^2$/day.

* * * * *